United States Patent
Dowle et al.

(10) Patent No.: US 6,177,425 B1
(45) Date of Patent: Jan. 23, 2001

(54) PYRROLOPYRROLONE DERIVATIVES

(75) Inventors: Michael Dennis Dowle; Harry Finch; Lee Andrew Harrison; Graham George Adam Inglis; Martin Redpath Johnson; Simon John Fawcett MacDonald; Pritom Shah, all of Stevenage (GB)

(73) Assignee: Glaxo Wellcome Inc., Research Triangle Park, NC (US)

( * ) Notice: Under 35 U.S.C. 154(b), the term of this patent shall be extended for 0 days.

(21) Appl. No.: 09/508,314

(22) PCT Filed: Sep. 7, 1998

(86) PCT No.: PCT/EP98/05743

§ 371 Date: May 5, 2000

§ 102(e) Date: May 5, 2000

(87) PCT Pub. No.: WO99/12934

PCT Pub. Date: Mar. 18, 1999

(30) Foreign Application Priority Data

Sep. 9, 1997 (GB) .................................................. 9719172

(51) Int. Cl.$^7$ .................. A61K 31/407; A61K 31/5355; A61P 11/00; C07D 487/04

(52) U.S. Cl. ....................... 514/234.5; 544/137; 544/144; 546/199; 548/248; 548/453

(58) Field of Search ............................. 544/144; 548/453; 514/234.5

(56) References Cited

U.S. PATENT DOCUMENTS 5,994,344 * 11/1999 Dowle et al. .................... 548/453

FOREIGN PATENT DOCUMENTS

| WO 9324519 | 12/1993 | (WO) . |
| WO 9521855 | 8/1995 | (WO) . |
| WO 9736903 | 10/1997 | (WO) . |

OTHER PUBLICATIONS

Coote et al, Chemical Abstracts, vol. 130, No. 223,259, 1999.*

* cited by examiner

Primary Examiner—Robert W. Ramsuer
(74) Attorney, Agent, or Firm—James P. Riek

(57) ABSTRACT

According to the invention there are provided Hexahydro-Pyrrolo[3,4-b]pyrrol-2-one compounds of formula (1), (relative stereochemistry indicated), wherein $R^1$, $R^2$ and $R^3$ are as defined in the specification. Compounds of formula (1) are useful inter alia in the treatment or chronic bronchitis.

13 Claims, No Drawings

PYRROLOPYRROLONE DERIVATIVES

This application is filed pursuant to 35 U.S.C. §371 as a United States National Phase Application of International Application No. PCT/EP98/05743 filed Sep. 7, 1998, which claims priority from GB9719172.0 filed Sep. 9, 1997.

The present invention relates to therapeutically active bicyclic compounds, processes for their manufacture, pharmaceutical formulations containing them and their use in chemotherapy. In particular, we have found a group of novel bicyclic compounds which are effective in treating inflammatory diseases.

Inflammation is a primary response to tissue injury or microbial invasion and is characterised by circulating leukocytes binding to and extravasation through vascular endothelium. Circulating leukocytes include neutrophils, eosinophils, basophils, monocytes and lymphocytes. Different forms of inflammation involve different types of infiltrating leukocytes.

The inflammatory process can be triggered in a number of ways, including by infection, tissue damage and autoimmune reactions. As part of the inflammatory process, neutrophils move from the bloodstream into the tissue at the site of tissue lesion. The neutrophils contain large numbers of different intracellular granules and when activated at the site of inflammation the contents of these granules are secreted into the tissue. The different granules contain a variety of enzymes and other proteins, many of which have antibacterial properties.

One of the enzymes found in the azurophilic granules is neutrophil elastase. Neutrophil elastase has a wide spectrum of activities in the body. For example, within the lung the enzyme increases mucus production and changes the cellular composition of the epithelium. The enzyme also causes vascular permeability changes within the microcirculation of many tissues and it is a potent destructive agent against a number of connective tissue components.

Although there are within the body endogenous inhibitors of elastase, including the anti-trypsin and the leukocyte protease inhibitor, elastase activity has been implicated in the pathogenesis of a number of disease states including inflammatory diseases of the airways, the joints and the skin. The enzyme is also responsible for some or most of the symptoms of acute respiratory distress syndrome (ARDS) and other acute inflammatory states brought about by trauma and/or sepsis.

We have now found a group of novel compounds which inhibit neutrophil elastase. These compounds are therefore of potential therapeutic benefit in the treatment and amelioration of symptoms of diseases where elastase activity is implicated.

Thus, according to one aspect of this invention, we provide a compound of the formula (I)

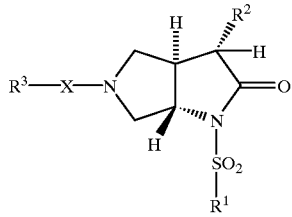

(relative stereochemistry indicated)
wherein:
$R^1$ represents $C_{1-6}$alkyl;
$R^2$ represents $C_{2-4}$alkyl or $C_{2-4}$alkenyl;
X represents CO or $SO_2$;
$R^3$ represents:
(a) $C_{2-8}$alkenyl $NR^4R^5$;
(b) phenyl substituted by $(CH_2)_aQ(CH_2)_bNR^4R^5$;
(c) a 5 or 6 membered heterocyclic aromatic ring containing 1 or 2 heteroatoms selected from N, S and O substituted by $(CH_2)_aQ(CH_2)_bNR^4R^5$;
(d) phenyl substituted by $NHCOC_{1-8}$alkyl;
(e) a group as defined in (b), (c), or (d) further substituted on the phenyl or heterocyclic ring by one or more groups selected from $C_{1-4}$alkyl, $C_{1-4}$alkoxy, halogen and nitro; or
(f) $C_{1-8}$alkyl$NR^4R^5$;
$R^4$ and $R^5$ independently represent hydrogen, $C_{1-8}$alkyl, $-(CH_2)_{1-4}CONR^6R^7$, $COC_{1-4}$alkyl or $(CH_2)_{0-2}$ Ph where Ph represents phenyl optionally substituted by one or more $C_{1-4}$alkyl or halogen groups or $NR^4 R^5$ together represents azetidinyl, pyrrolidinyl, piperidinyl, azepinyl, morpholinyl, piperazinyl or $N-C_{1-6}$alkyl-piperazinyl or such a heterocyclic ring optionally substituted by one or more $C_{1-4}$alkyl, $CONR^6R^7$ or $COOR^6$ groups;
Q represents a bond, S, O or $NR^8$;
a represents 0 to 4 and b represents 2 to 4 save that a+b lies in the range 2 to 6 except when Q represents a bond in which case b may also represent 0 or 1 and a+b may lie in the range 0 to 6;
$R^6$, $R^7$ and $R^8$ independently represent hydrogen or $C_{1-4}$alkyl; and salts and solvates thereof (hereinafter "compounds of the invention").

Formula (I) shows the relative stereochemistry of the chiral centres. The invention embraces compounds of the invention in racemic form as well as in a form in which one enantiomer predominates or is present exclusively. Generally, we prefer to provide a compound of formula (I) in enantiomerically pure form, most particularly the enantiomer having absolute stereochemistry as illustrated in formula (I).

The present invention also covers the physiologically acceptable salts of the compounds of formula (I). Suitable inorganic and organic acid salts include the hydrochloride and tartrate.

When used herein "alkyl" includes branched as well as straight chain alkyl and may also include cycloalkyl when 3 or more carbon atoms are present.

When $R^3$ represents $C_{2-8}$alkenyl$NR^4R^5$, examples include $CH=CHCH_2NR^4R^5$.

When $R^3$ represents phenyl substituted by $NHCOC_{1-8}$alkyl, examples include phenyl substituted by NHCOMe.

When $R^3$ represents $C_{1-8}$alkyl$NR^4R^5$, examples include $(CH_2)_3NR^4R^5$.

When $R^3$ represents a substituted 5 or 6 membered heterocyclic aromatic ring, examples of heterocycles include furan, pyrrole, thiophene, imidazole, thiazole, isoxazole, pyrazole, pyrazine and pyridine.

When $R^4$ and $R^5$ independently represent $C_{1-8}$alkyl, examples include methyl and cyclopropyl.

When $R^4$ and $R^5$ independently represent $(CH_2)_{1-4}CONR^6R^7$ examples include $CH_2CONMe_2$.

When $R^4$ and $R^5$ independently represent $COC_{1-4}$alkyl, examples include COMe.

Suitable $R_1$ alkyl groups include methyl, ethyl and propyl.

We prefer $R^1$ to represent methyl or ethyl, especially methyl.

We prefer $R^2$ to represent isopropyl or propyl, especially isopropyl.

We prefer X to represent CO.

We prefer $R^3$ to represent (a) $C_{2-8}$alkenyl $NR^4R^5$;

(b) phenyl substituted by $(CH_2)_aQ(CH_2)_bNR^4R^5$;

(c) a 5 or 6 membered heterocyclic aromatic ring containing 1 or 2 heteroatoms selected from N, S and O substituted by $(CH_2)_aQ(CH_2)_bNR^4R^5$;

(d) phenyl substituted by $NHCOC_{1-8}$alkyl; or (e) a group as defined in (b), (c), or (d) further substituted on the phenyl or heterocyclic ring by one or more groups selected from $C_{1-4}$alkyl, $C_{1-4}$alkoxy, halogen and nitro.

We particularly prefer $R^3$ to represent:

(a) $C_{2-8}$alkenyl $NR^4R^5$;

(b) phenyl substituted by $(CH_2)_aQ(CH_2)_bNR^4R^5$;

(c) a 5 or 6 membered heterocyclic aromatic ring containing 1 or 2 heteroatoms selected from N, S and O substituted by $(CH_2)_aQ(CH_2)_bNR^4R^5$; or (d) a group as defined in (b) or (c) further substituted on the phenyl or heterocyclic ring by one or more groups selected from $C_{1-4}$alkyl, $C_{1-4}$alkoxy, halogen and nitro.

We prefer $R^4$ and $R^5$ independently to represent hydrogen or $C_{1-8}$alkyl or for $NR^4R^5$ to represent pyrrolidinyl, piperidinyl, morpholinyl or piperazinyl optionally N-substituted by $C_{1-8}$alkyl or phenyl (optionally substituted by halogen or $C_{1-4}$alkyl).

We prefer Q to represent a bond and for a+b to represent 1 or 2.

The potential for compounds of the invention to inhibit neutrophil elastase activity may be demonstrated, for example, using the following in vitro and in vivo assays:

In vitro Assays of Human Neutrophil Elastase

Assay contents:

50 mM Tris/HCl (pH 8.6)

150 mM NaCl 11.8 nM purified human neutrophil elastase

Suitable concentrations of compound under test diluted with water from a 10 mM stock solution in dimethylsulphoxide. Values above are final concentrations after the addition of substrate solution (see below).

The mixture above is incubated for fifteen minutes at 30° C. at which time the remaining elastase activity is measured for 10 minutes in a BioTek 340i plate-reader, after the addition of 0.6 mM MeO-succinyl-alanyl-alanyl-prolyl-valyl-p-nitroanilide. The rate of increase in absorbance at 405 nm is proportional to elastase activity. Enzyme activity is plotted against concentration of inhibitor and an $IC_{50}$ determined using curve fitting software.

In vivo Activity of Inhibitors of Human Neutrophil Elastase: An Oral in vivo Model Using IL-8 Induced Lung Infiltrates for the Assessment of Intracellular Elastase Inhibition Adult hamsters (100–150 g) are randomised into groups (n=4) and fasted overnight. Under gaseous anaesthetic (3% isofluorane) animals are dosed orally with 1 mL/100 g water as vehicle or containing predissolved compounds. Either at the same time, or subsequently under anaesthetic, animals are dosed intratracheally with 1 ug recombinant human IL-8 in 100 uL sterile saline. Six hours after IL-8 dosing animals are sacrificed using intraperitoneal pentobarbitone. The lungs are lavaged with 2×2.5 mL sterile saline and femurs are removed by dissection.

Intracellular elastase is prepared from neutrophils collected by lavage and from femoral bone marrow. This is achieved by sonication of the neutrophils and centrifugation to yield intracellular granules. These are disrupted by freeze/thawing and sonication. Elastase and myeloperoxidase assays are then performed on these samples to assess the efficacy of the compounds and to normalise for neutrophil recovery.

Accordingly, the compounds of the invention are of potential therapeutic benefit in the treatment and amelioration of symptoms of diseases where elastase activity is implicated. Such diseases particularly include bronchitis, including chronic bronchitis. Also any chronic obstructive pulmonary disease (COPD).

Examples of disease states in which the compounds of the invention have potentially beneficial effects include inflammatory diseases of the respiratory tract such as bronchitis (including chronic bronchitis), bronchiectasis, asthma and hyper-reactivity states of the lung, acute respiratory distress syndrome and septic shock, inflammatory or destructive conditions of the lung such as emphysema and cystic fibrosis and inflammatory or destructive conditions of external tissue such as skin diseases (e.g. lupus and psoriasis) and periodontal disease including gingivitis.

Further examples of disease states and conditions in which compounds of the invention have potentially beneficial effects include wound healing and treatment of burns, cardiovascular diseases such as myocardial infarction and stroke, peripheral vascular disease including intermittent claudication, atherosclerosis, reperfusion injury, cardiovascular changes occurring during cardiopulmonary bypass surgery and septicemia.

Compounds of the invention may also be useful in the treatment of connective tissue disorders such as rheumatoid arthritis, osteoarthritis and spondylitis and inflammatory conditions of the kidney such as glomerulonephritis.

They may also be useful in the treatment of certain leukemias including acute myelogenous leukemia, acute myelomonocytic leukemia and the chronic monocytic leukemias and in prevention or inhibition of metastasis of solid tumours e.g. lung, breast, prostate and stomach cancers and melanomas.

A particular aspect of the present invention is the use of compounds of formula (I) in the treatment of chronic bronchitis. Chronic bronchitis is a condition which results from the exposure of the airway surface to noxious chemicals or agents or is secondary to another disease. The symptoms of the condition are caused by the excessive secretion of mucus onto the surface of the airways. This excess mucus cannot be cleared effectively and the result is reduced gas exchange within the lungs resulting in laboured breathing and hypoxemia, recurrent microbial infections and persistent cough associated with the expectoration of mucoid material. The proposed mechanism for the excessive secretion of mucus involves the recruitment of neutrophils into the airways following the exposure of the epithelium to irritant materials; the neutrophils secrete elastase onto the surface of the airways and the enzyme brings about both an increase in the amount of mucus secreted onto the airway surfaces and a dramatic change in the cellular composition of the airway epithelium. Inhibition of elastase activity by the administration of compounds of this invention is therefore an approach to the treatment of chronic bronchitis. Reduced lung function in COPD (eg in chronic bronchitics with airflow obstruction) is also due to elastase mediated lung damage leading to airway narrowing and inflammation. Thus an elastase inhibitor will improve lung function.

As indicated above, compounds of the invention are useful in human or veterinary medicine, in particular as inhibitors of the enzyme neutrophil elastase.

Thus, there is provided as a further aspect of the present invention a compound of formula (I) or a physiologically acceptable salt or solvate thereof for use in human or veterinary medicine, particularly in the treatment of conditions where elastase activity is implicated such as chronic bronchitis.

It will be appreciated that references herein to treatment extend to prophylaxis as well as the treatment of established conditions.

According to another aspect of the invention, there is provided the use of a compound of formula (I) or a physiologically acceptable salt or solvate thereof for the manufacture of a medicament for the treatment of conditions where elastase activity is implicated, particularly in chronic bronchitis.

In a further or alternative aspect there is provided a method for the treatment of a human or animal subject with a condition caused or mediated by elastase activity which method comprises administering to said human or animal subject an effective amount of a compound of formula (I) or a physiologically acceptable salt or solvate thereof.

The compounds according to the invention may be formulated for administration in any convenient way, and the invention therefore also includes within its scope pharmaceutical compositions for use in therapy, comprising a compound of formula (I) or a physiologically acceptable salt or solvate thereof in admixture with one or more physiologically acceptable diluents or carriers.

There is also provided according to the invention a process for preparation of such a pharmaceutical composition which comprises mixing the ingredients.

The compounds according to the invention may, for example, be formulated for oral, buccal, parenteral, topical or rectal administration.

Tablets and capsules for oral administration may contain conventional excipients such as binding agents, for example syrup, acacia, gelatin, sorbitol, tragacanth, mucilage of starch or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or toxicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

By topical administration as used herein, we include administration by insufflation and inhalation. Examples of various types of preparation for topical administration include ointments, creams, lotions, powders, pessaries, sprays, aerosols, capsules or cartridges for use in an inhaler or insuflator or drops (e.g. eye or nose drops).

Ointments and creams may, for example, be formulated with an aqueous or oily base with the addition of suitable thickening and/or gelling agents and/or solvents. Such bases may thus, for example, include water and/or an oil such as liquid paraffin or a vegetable oil such as arachis oil or castor oil or a solvent such as a polyethylene glycol. Thickening agents which may be used include soft paraffin, aluminium stearate, cetostearyl alcohol, polyethylene glycols, microcrystalline wax and beeswax.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents or suspending agents.

Spray compositions may be formulated, for example, as aqueous solutions or suspensions or as aerosols delivered from pressurised packs, with the use of a suitable propellant, e.g. dichlorodifluoromethane, trichlorofluoromethane, dichlorotetrafluoroethane, 1,1,1,2,3,3,3-heptafluoropropane, 1,1,1,2-tetrafluorethane, carbon dioxide or other suitable gas.

Capsules and cartridges for use in an inhaler or insufflator, of for example gelatin, may be formulated containing a powder mix of a compound of the invention and a suitable powder base such as lactose or starch.

The pharmaceutical compositions according to the invention may also be used in combination with other therapeutic agents, for example anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), lung surfactants and/or antimicrobial and anti-viral agents. The compositions according to the invention may also be used in combination with gene replacement therapy.

The invention thus provides, in a further aspect, a combination comprising a compound of formula (I) or a physiologically acceptable salt or solvate thereof together with another therapeutically active agent.

The combination referred to above may conveniently be presented for use in the form of a pharmaceutical formulation and thus pharmaceutical formulations comprising a combination as defined above together with a pharmaceutically acceptable carrier thereof represent a further aspect of the invention.

The individual components of such combinations may be administered either sequentially or simultaneously in separate or combined pharmaceutical formulations. Appropriate doses of known therapeutic agents will be readily appreciated by those skilled in the art.

The compound of the invention may conveniently be administered in amounts of, for example, 0.01 to 50 mg/kg body weight, suitably 0.05 to 25 mg/kg body weight orally, one or more times a day. The precise dose will of course depend on the age and condition of the patient, the particular route of administration chosen, and the disease being treated. The compound is preferably administered orally for the treatment of bronchitis. Other routes of administration may be needed for other indications, for instance i.v. for ARDS.

The compounds of the invention have useful duration of action.

The compounds of formula (I) and salts and solvates thereof may be prepared by the methodology described hereinafter, constituting a further aspect of this invention.

A process according to the invention for preparing a compound of formula (I) comprises:

(i) condensation of a compound of formula (II):

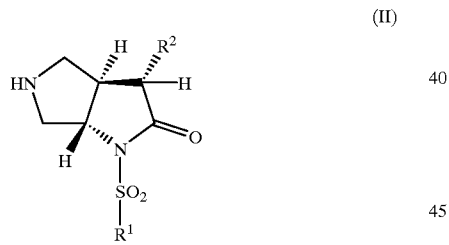

(II)

(relative stereochemistry indicated)
with a compound $R^3COOH$ or $R^3XY$, where Y is a reactive group such as halogen, e.g. chlorine, or a protected derivative thereof; or (ii) sulphonylation of a compound of formula (III):

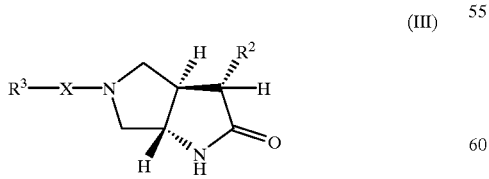

(III)

(relative stereochemistry indicated)
or a protected derivative thereof,
with a compound $YO_2SR^1$ wherein Y is a reactive group such as halogen, e.g. chlorine; or (iii) cyclising a compound of formula (IV):

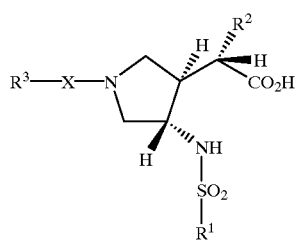

(IV)

(relative stereochemistry indicated)
or a carboxylic acid ester thereof; or (iv) oxidation of a corresponding compound of formula (V)

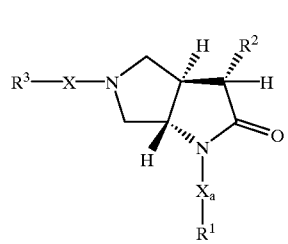

(V)

(relative stereochemistry indicated)
wherein $X_a$ is sulphur or SO; or (v) reaction of a corresponding compound of formula (VI)

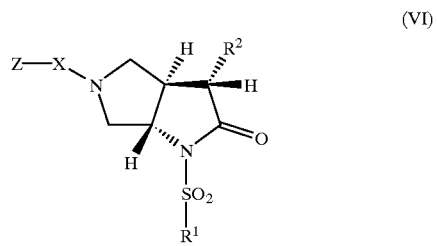

(VI)

(relative stereochemistry indicated)
wherein Z represents
(a) $C_{2-8}$alkenyl-L
(b) phenyl substituted by $(CH_2)_aQ(CH_2)_b$-L;
(c) a 5 or 6 membered heterocyclic aromatic ring containing 1 or 2 heteroatoms selected from N, S and O substituted by $(CH_2)_aQ(CH_2)_b$-L, or
(d) a group as defined in (b) or (c) further substituted by one or more groups selected from $C_{1-4}$alkyl, $C_{1-4}$alkoxy, halogen and nitro; or
(e) $C_{1-8}$alkyl-L
and L represents a leaving group, save that when Q represents a bond, a and b do not both represent 0;
with a compound of formula $R^4R^5NH$; or (vi) reduction of the product of reaction of a corresponding compound of formula (VII)

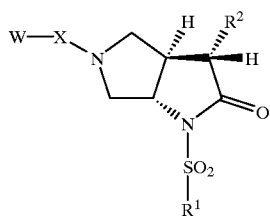

(VII)

(relative stereochemistry indicated)
wherein W represents:
(a) $C_{2-7}$alkenyl-CHO;
(b) phenyl substituted by $(CH_2)_aQ(CH_2)_c$ CHO;
(c) a 5 or 6 membered heterocyclic aromatic ring containing 1 or 2 heteroatoms selected from N, S and O substituted by $(CH_2)_aQ(CH_2)_c$-CHO;
(d) a group as defined in (b) or (c) further substituted by one or more groups selected from $C_{1-4}$alkyl, $C_{1-4}$alkoxy, halogen and nitro; or
(e) $C_{1-7}$alkylCHO
wherein c represents b-1 save that it may not be less than zero,
with a compound of formula $R^4R^5NH$; or
(vii) conversion of one compound of formula (I) into another compound of formula I; or
(viii) deprotecting a compound of formula (I) which is protected; or
(viii) purifying one enantiomer of the compound of formula (I) from a mixture of enantiomers;
and where desired or necessary converting a resultant free base compound of formula I into a physiologically acceptable salt form or vice versa or converting one salt form into another physiologically acceptable salt form.

Process (i)

The condensation reaction with $R^3COOH$ is suitably carried out in the presence of a coupling agent such as 1-(3-N,N-dimethylaminopropyl)-3-ethylcarbodiimide, and a solvent such as dichloromethane, DMF or tetrahydrofuran at a temperature of suitably between 0° C. and ambient. It will be appreciated that as an alternative to using $R^3COOH$, acid derivatives such as the acid chloride, activated ester, acid anhydride, or a mixed anhydride may be used. Reaction conditions will be modified accordingly, for instance by inclusion of a base. If one or both $R^3$, $R^4$ represents hydrogen, it will generally be preferred to protect the nitrogen, e.g. with BOC.

With $R^3XY$ the reaction is suitably carried out in the presence of a base such as triethylamine and a solvent such as DCM, suitably at 0° C.—ambient.

Process (ii)

The sulphonylation reaction is suitably carried out in the presence of LHMDS, or NaH, in a solvent such as tetrahydrofuran at a temperature of suitably between −78° C. to 0° C.

A nitrogen in the $R^3$ sidechain may require protecting, e.g. with BOC.

Process (iii)

The cyclisation reaction is suitably carried out in the presence of 2-chloro-1-methylpyridinium iodide, or 1-(3-N, N-dimethylaminopropyl)-3-ethylcarbodiimide (EDC), in a solvent such as dichloromethane, at a temperature of suitably 0° C.—reflux. This reaction may also be performed using a carboxylic acid thioester derivative of the compound of formula (IV).

Process (iv)

This oxidation reaction may be carried out in conventional manner such as by peracid oxidation.

Process (v)

Leaving groups include halogen (e.g. chlorine, bromine) mesylate and tosylate.

This reaction may be performed by combining the reactants optionally in the presence of a base such as triethylamine or potassium carbonate in an inert aprotic solvent such as DMF or MeCN.

Process (vi)

This reaction will take place on combining the reagents in an inert solvent, e.g. DCM at ambient or elevated temperature.

Reduction can be performed in situ using a conventional mild reducing agent such as $NaBH_3CN$ or $NaBH(OAc)_3$.

Process (vii)

Conversion may be performed by conventional methods. For example, compounds of formula I in which $R^3$ represents phenyl substituted by $NHCOC_{1-8}$alkyl may be prepared by acylating a corresponding compound of formula I in which $R^3$ represents phenyl substituted by $NH_2$.

Process (viii)

Protecting groups, especially nitrogen protecting groups, and means for deprotection are described in T W Greene "Protective Groups in Organic Synthesis", 2nd Ed (1991) J Wiley & Sons.

Process (ix)

Purification of a single enantiomer may be achieved by conventional methods such as chiral chromatography (e.g. chiral HPLC) and crystallisation with a homochiral acid (e.g. tartaric acid).

Physiologically acceptable acid salts such as the hydrochloride or tartrate may be prepared by treating a basic compound of formula (I) with the desired acid.

Intermediate compounds of formula (II) may conveniently be prepared according to the methodology in Scheme I below (compounds are drawn with relative stereochemistry):

Scheme 1

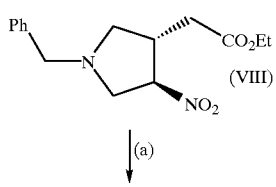

(VIII)

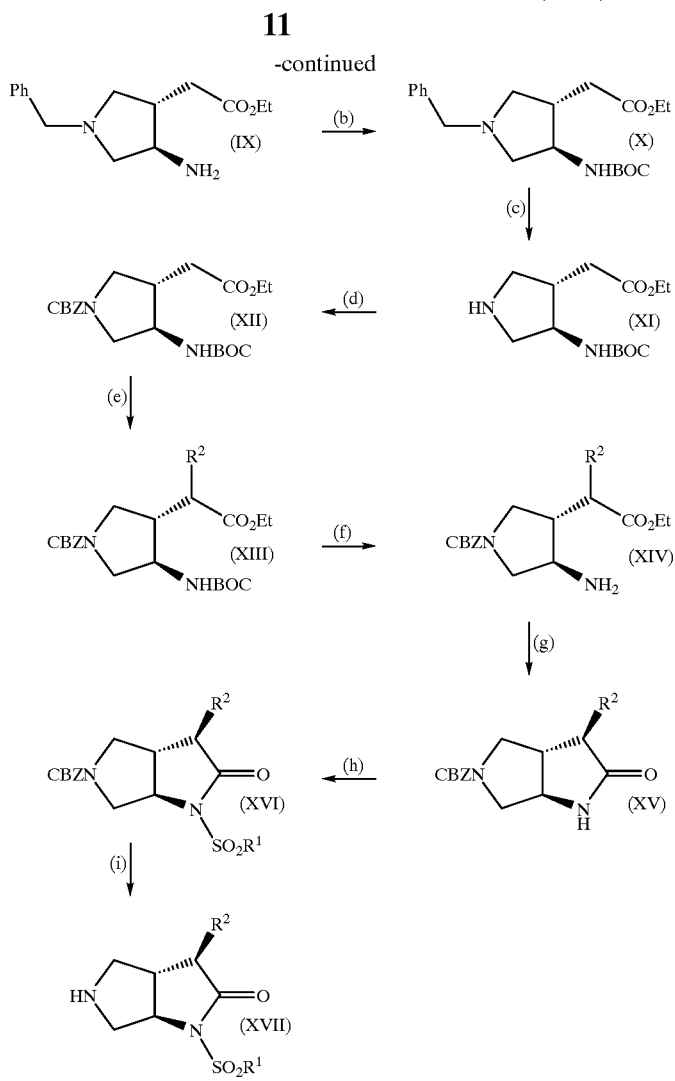

Step a
This is a standard nitro group reduction which may be achieved using hydrogen in the presence of a metal catalyst, e.g. palladium supported on carbon, in a suitable solvent such as ethanol.

Step b
This is a conventional protection reaction which may be performed by reacting with $BOC_2O$ in the presence of a base, e.g. triethylamine, in an inert solvent such as acetonitrile or dichloromethane.

Step c
This is a conventional deprotection reaction which may be achieved by reacting with hydrogen or ammonium formate in the presence of a metal catalyst, e.g. palladium supported on carbon, in a suitable solvent such as ethanol.

Step d
This is a conventional protection reaction which may be performed by reacting with benzyl chloroformate in the presence of a base, e.g. triethylamine, in an inert solvent such as acetonitrile or dichloromethane.

Step e
This alkylation reaction may be achieved by the sequential reactions with a strong base, e.g. LHMDS, in the presence of DMPU in an inert solvent such as THF or diethyl ether at −70° C., followed by alkyl halide, e.g. bromide or iodide, at −70° C.—room temperature.

Step f
This is a conventional deprotection reaction which may be performed by reacting with an acid, e.g. trifluoroacetic acid or hydrogen chloride in a suitable solvent such as dichloromethane or dioxane.

Step g
This cyclisation may be achieved using t-butyl magnesium chloride in the presence of TMEDA in an inert solvent such as THF or diethyl ether. The use of TMEDA is optional.

Step h
This standard sulphonylation reaction may be achieved by sequential reactions with a strong base, e.g. LHMDS, in an inert solvent such as THF or diethyl ether at −70°–0° C., followed by the appropriate alkylsulphonylhalide (eg methanesulfonyl chloride) at −70° C.—room temperature.

Step i
This conventional deprotection reaction can be achieved by reacting with hydrogen in the presence of a metal catalyst, e.g. palladium supported on carbon, and a proton source, e.g. ethereal hydrogen chloride, in a suitable solvent such as ethyl acetate or ethanol. The use of a proton source is optional.

A chiral resolution step (see main process (viii) above) may also be introduced into Scheme 1 at a convenient point in order to produce enantiomerically pure products, if desired.

Certain compounds of formula (XVII) in which $R^2$ represents isopropyl may alternatively be prepared by following an alternative Scheme 2 from compounds of formula (XII) (compounds are drawn with relative stereochemistry):

is given in Scheme 3 (compounds are drawn with relative stereochemistry):

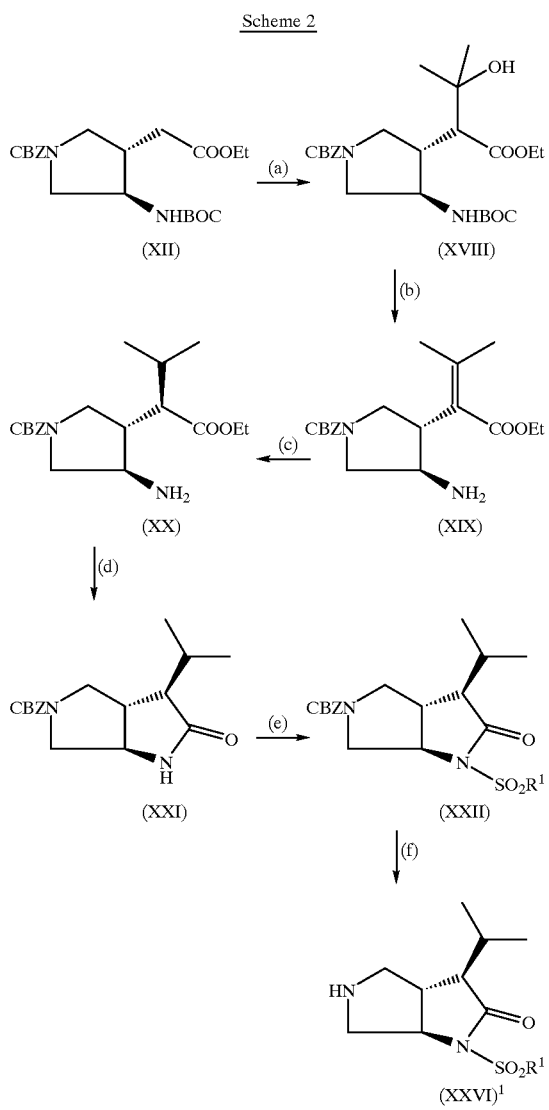

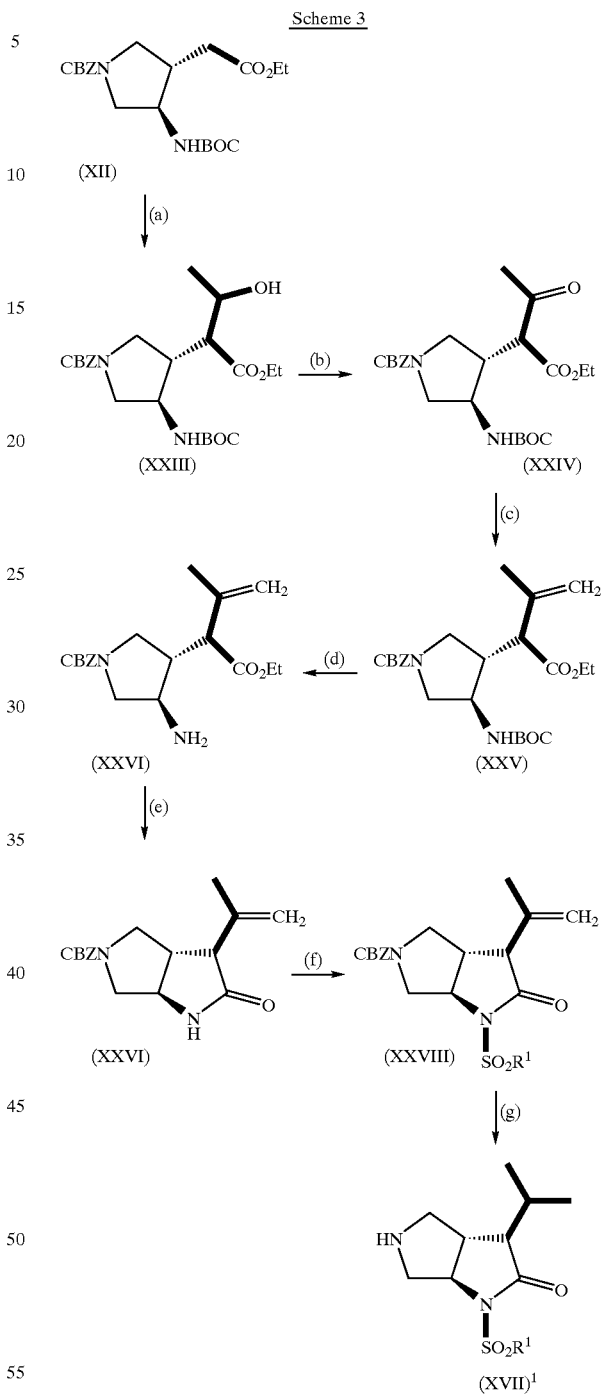

Step (a)

For this reaction, the anion of the compound of formula (XII) is first prepared by treatment with a strong base, e.g. LHMDS, followed by treatment with acetone.

Step (b)

Standard dehydration conditions may be used for this reaction, e.g. treatment with concentrated sulphuric acid. These conditions will remove the BOC deprotecting group, otherwise the deprotection can be performed as an additional step.

Step (c)

This is a reduction reaction which will be performed under mild conditions so as not to remove the CBZ protecting group. Hydrogenation over Pd/C in ethanol or ethyl acetate for a short period of time (eg <1 hr) will be suitable.

Steps (d)–(f)

These processes are analogous to Scheme I, steps (g)–(i).

A further alternative method for preparation of compounds of formula (XVII) in which $R^2$ represents isopropyl Step (a)

For this reaction, the anion of compound of formula (XII) is prepared by treatment with a strong base, e.g. LHMDS, followed by treatment with acetaldehyde.

Step (b)

This oxidation may be suitably carried out under nitrogen using Swern oxidation conditions, e.g. oxalyl chloride and DMSO at −80°–0° in dichloromethane, followed by triethylamine.

Step (c)

This methylenation may be achieved using Tebbe reaction conditions, e.g. m-chlorobis($h^5$-2,4-cyclopentadien-1-yl)(dimethylaluminium)-m-methylenetitanium in THF at around 0°-room temperature.

Step (d)

This standard deprotection may be performed using an acid, e.g. trifluroacetic acid or hydrogen chloride, in a suitable solvent such as dichloromethane or dioxane.

Step (e)

This cyclisation may be achieved using t-butyl magnesium chloride in an inert solvent such as THF or diethyl ether.

Step (f)

This process is analogous to Scheme 1, step (h).

Step (g)

This is a conventional deprotection reaction which may be achieved by reacting with hydrogen in the presence of a metal catalyst catalyst, e.g. palladium on carbon, in a suitable solvent such as ethanol.

In Schemes 1, 2 and 3, a diastereomeric separation may be necessary to obtain the compound of desired stereochemistry.

The protecting groups CBZ and BOC used in Schemes 1, 2 and 3 are preferred illustrations and alternative protecting groups can be contemplated.

The route shown in Scheme 2 may also be followed for the preparation of compounds having different $R^2$, especially bulky $R^2$. A different ketone reagent will then be used in step (a).

Scheme 3 may also be adapted to produce compounds of formula (XVII) having other branched $R^2$ alkyl or alkenyl sidechains.

The intermediate compounds of formula (III) may be prepared by reacting a deprotected compound of formula (XV) from Scheme 1 with $R^3$COOH or $R^3$XY in the manner described above in relation to main process (i) above.

The intermediate compounds of formula (IV) may be prepared from a compound of formula (XIV) in an analogous manner to that described above for preparing a compound of formula (III) from a compound of formula (XV) together with main process (ii) above.

Compounds of formula (V) wherein $X_a$ represents S may be prepared by reaction of a corresponding compound of formula (III) with a compound of formula $R^1SSR^1$ under standard conditions for nucleophilic displacement in the presence of base. Compounds of formula (V) wherein $X_a$ represents SO may be prepared by peracid oxidation of a corresponding compound wherein $X_a$ represents S.

Compounds of formula (VI) and (VII) may be prepared from compounds of formula (II) following conventional methods known per se.

The compound of formula (VIII) may be prepared by the method of Archille Barco et al (1992) J. Org. Chem. 57, 6279.

Compounds of formula R₃COOH and $R^3$XY are either known or may be prepared by conventional methods known per se.

It will be apparent to a person skilled in the art that the above synthetic processes for the preparation of compounds of formula (I) may be modified so as to include or omit protecting groups or so as to use alternative protecting groups (for example those described in T W Greene "Protective Groups in Organic Synthesis", 2nd Ed (1991) J Wiley & Sons) in the course of routine optimisation of experimental conditions.

Certain of the intermediate compounds herein described are novel and form an important aspect of the invention. We provide intermediates as racemic mixtures or in the form of a purified single enantiomer.

Processes for preparation of intermediates are also provided as an aspect of this invention.

The following non-limiting Example illustrates the present invention.

| ABBREVIATIONS | |
|---|---|
| BOC | t-butyloxycarbonyl |
| CBZ | Benzyloxycarbonyl |
| (BOC)₂O | Di-tert-butyldicarbonate |
| THF | Tetrahydrofuran |
| LHMDS | Lithium bis (trimethyisilyl)amide |
| DMPU | 1,3-dimethyl-3,4,5,6-tetrahydro 2 (1H)-pyrimidinone |
| DMAP | 4-dimethylaminopyridine |
| DMF | Dimethylformamide |
| EDC | 1-(3-N,N-dimethylaminopropyl)-3-ethylcarbodiimide |
| DCM | dichloromethane |
| DMSO | dimethylsulphoxide |
| TMEDA | tetramethylethylene diamine |

INTERMEDIATES

Intermediate I rel-(3S,4R)-(1-Benzyl-4-nitro-pyrrolidin-3-yl)-acetic acid ethyl ester This compound was prepared by the method of Archille Barco et al J.Org.Chem.1992, 57, 6279 as a medium brown oil. Tlc silica (cyclohexane:ethyl acetate:3:1) Rf 0.26.

Intermediate II rel-(3S,4R)-(4-Amino-1-benzyl-pyrrolidin-3-yl)-acetic acid ethyl ester A solution of Intermediate I (397 g) in absolute ethanol (1.4 l) was reduced at room temperature with stirring over a platinum/carbon catalyst (5% 115 g) under a hydrogen atmosphere. The reaction proceeded to completion over 5 h ($H_2$ uptake 99.7 l). The reaction mixture was filtered through celite and evaporated in vacuo to give the title compound as a light brown oil (303 g).

Tlc Silica, cyclohexane:ethyl acetate (3:1); Rf 0.15.

Intermediate III rel-(3S,4R)-(1-Benzyl-4-tert-butoxycarbonylamino-pyrrolidin-3-yl)-acetic acid ethyl ester A solution of (BOC)₂O (289 g) in acetonitrile (1.5 l) was added below 25° C. with stirring over 25 min to a solution of Intermediate II (288.8) and triethylamine (111.2 g) in acetonitrile (1.5 l). After 2.5 days the solvent was removed in vacuo and the resultant brown oil partitioned between ethyl acetate (2.5 l) and water (2 l). The aqueous layer was further extracted with ethyl acetate (2 l). The combined organics were washed with brine, dried ($MgSO_4$), filtered and evaporated. The residual light brown solid was triturated with ether and then collected by filtration. The title compound was obtained as a white solid (233 g). Tlc Silica, hexane:ethylacetate (3:1); Rf 0.27.

Intermediate IV rel-(3S,4R)-(4-tert-Butoxycarbonylamino-pyrrolidin-3-yl)-acetic acid ethyl ester A solution of Intermediate III (100 g) in absolute ethanol (1.25 l) was reduced over palladium on carbon catalyst (10%, 20 g) under a hydrogen atmosphere at room temperature and with stirring (Hydrogen uptake 7.5l). After 20 h the reaction mixture was filtered through hyflo and evaporated in vacuo to give the title compound as a colourless oil (71 g) which crystallised to a white solid on standing. Tlc silica (dichloromethane; ethanol; ammonia 80:20:2) Rf 0.4.

Intermediate V rel-(3S,4R)-3-tert-Butoxycarbonylamino-4-ethoxycarbonylmethyl-pyrrolidine-1-carboxylic acid benzyl ester Triethylamine (156 ml) was added slowly to a cooled solution of Intermediate IV (100.7 g) and benzyl chloroformate (74 ml) in dichloromethane (3 l) at 10° C. with stirring. The temperature during the addition was maintained below 15° C. The reaction mixture was stirred overnight and then washed with water (3 l). The solvent was removed in vacuo and the residual oil purified by chromatography on silica (Merck 9385) eluting with hexane:ethyl acetate (3:1). The resultant white solids were combined and triturated with hexane:ethyl acetate (2:1) (400 ml), to give the title compound 155 g. Mass spec. (found) $MH^+$=407 (calc) $MH^+$=407.

Intermediate VI rel-(3S,4R)-3-tert-Butoxycarbonylamino-4-(1-ethoxycarbonyl-but-3-enyl)-pyrrolidine-1-carboxylic acid benzyl ester A solution of lithium bis (trimethylsilyl) amide in tetrahydrofuran (1M, 80 ml) was added dropwise over 1 h with stirring under a nitrogen atmosphere at –70° C. to a solution of the Intermediate V (9.8 g) in a mixture of dry tetrahydrofuran (54 ml) and 1,3-dimethyl-3,4,5,6-tetrahydro 2 (1H) pyrimidinone (120 ml). After a further 1 h allyl iodide (2.8 ml) was added dropwise over 10 min and the mixture was stirred below –70° C. for 2 h. The reaction was quenched with saturated aqueous ammonium chloride (30 ml) which was added dropwise over 30 min. The mixture was extracted with ethyl acetate (4×100 ml). The combined extracts were dried ($MgSO_4$), filtered and evaporated in vacuo to give an orange oil (26 g). The oil was partitioned between toluene (200 ml) and water (100 ml). The organics were washed with water (2×100 ml) and brine (80 ml), dried ($Na_2SO_4$), filtered and evaporated to give a clear orange oil (15 g). Purification of this oil by flash column chromatography on silica (Merck 9385) using gradient elution [ethyl acetate:hexane from (1:9) to (2:3)]. The title compound was thereby obtained as a white crystalline solid (8.6 g). Mass spec $MH^+$ (found) 447 $MH^+$ (calc) 447.

Intermediate VII rel-(3R,4S)-3-Amino-4-(1-ethoxycarbonyl-but-3-enyl)-pyrrolidine-1-carboxylic acid benzyl ester Intermediate VI (5 g) was dissolved in 4M hydrogen chloride in dioxan (53 ml) at room temperature. The solution was stirred for 3 h and evaporated. The residue was partitioned between water (100 ml) and ether (50 ml). The aqueous layer was washed with ether (50 ml) and then basified with saturated aqueous sodium hydrogen carbonate (100 ml). The mixture was extracted with ethyl acetate (3×50 ml). The combined extracts were dried ($Na_2SO_4$) filtered and evaporated to give the title compound as a clear, pale yellow, viscous oil (3.7 g). Mass spec $MH^+$ (found) 347 $MH^+$ (calc) 347.

Intermediate VIII rel-(3R,3aS,6aR)-3-Allyl-2-oxo-hexahydro-pyrrolo[3,4-b]pyrrole-5-carboxylic acid benzyl ester A solution of Intermediate VII (3.5 g) in a mixture of dry tetrahydrofuran (35 ml) and dry tetramethylethylenidiamine (35 ml) was cooled to 5° C. A solution of t-butyl magnesium chloride (1M, 32 ml) in tetrahydrofuran was added over 25 min and the mixture was allowed to warm to room temeperature over 1.5 h. After a further 1.5 h the reaction was quenched with saturated aqueous ammonium chloride (10 ml). Chilled 2M hydrochloric acid (100 ml) was then added with cooling. The resultant mixture was acidified (pH1–2) using concentrated hydrochloric acid (40 ml). The mixture was extracted with ethyl acetate (3×100 ml). The combined extracts were washed with brine, dried ($Na_2SO_4$), filtered and evaporated to give the title compound as a white crystalline solid (3 g). Mass spec $MH^+$ (found) 301 $MH^+$ (calc) 301.

Intermediate IX rel-(3R,3aS,6aR)-3-allyl-methanesulfonyl-2-oxo-hexahydropyrrolo[3,4-b]pyrrole-5-carboxylic acid benzyl ester A solution of lithium hexamethyldisilazide in tetrahydrofuran (1M, 13 ml) was added at –10° C. over 10 min to a stirred solution of Intermediate VIII (3 g). After 5 min the reaction was allowed to warm to around 0° C., at which temperature it was held for 35 min. The mixture was recooled to –70° C. and methanesulphonyl chloride (1.93 ml) was added dropwise over 15 min. After a further 3.5 h the reaction was quenched with saturated aqueous ammonium carbonate (20 ml) at below –50° C. It was then allowed to attain ambient, when it was diluted with water (100 ml) and extracted with ethyl acetate (3×100 ml). The combined extracts were washed with brine (100 ml), dried ($Na_2SO_4$), filtered and evaporated. The resultant oil was purified by flash column chromatography on silica using gradient elution. The eluent was initially ethyl acetate hexane (4:1) and increased in palarity to ethyl acetate:hexane (5:1). The title compound was obtained as a viscous gum/glass (3.1 g). Mass spec $MH^+$ (found) 379 $MH^+$ (calc) 379 $MNH_4^+$ (found) 396 $MNH_4^+$ (found) 396.

Intermediate X rel-(3R,3aS,6aR)-1-Methanesufonyl-3-propyl-hexahydro-pyrrolo[3,4-b]pyrrol-2-one hydrochloride A solution of Intermediate IX (3 g) in ethyl acetate (150 ml) containing ethereal hydrogen chloride (1.0M, 12 ml) was stirred over 5% palladium on activated carbon (wet 1.5 g) under a hydrogen atmosphere. After 5 h more catalyst (0.5 g) was added and the reaction was stirred for a further 16 h. (Hydrogen uptake 470 ml). The reaction mixture was diluted with an equal volume of absolute ethanol and then filtered through celite. The filtrate was evaporated, redissolved in a mixture of ethyl acetate and dichloromethane (1:10, 100 ml) and extracted with water (2×50 ml). The combined extracts were washed with ethyl acetate (50 ml), basified with saturated aqueous sodium hydrogen carbonate and extracted with dichloromethane (4×50 ml). The combined extracts were dried ($Na_2SO_4$) filtered and evaportated to give a pale yellow foam (1.2 g). Ethereal hydrogen chloride (1.0M, 5 ml) was added and the mixture reevaporated to give the title compound as a glass. Tlc silica (dichloromethane:ethanol:ammonia, 100:8:1) Rf 0.1.

Intermediate XI

4-(Piperidin-1-yl)-but-2-enoic Acid Anhydride Dihydrochloride

Oxalyl chloride (4.2 ml) was added to a stirred solution of 4-(piperidin-1-yl)-but-2-enoic acid hydrochloride (10 g) in dichloromethane (200 ml). Dimethylformamide (2 drops) was then added. The resultant suspension was stirred for 4 h and then concentrated to ~25 ml. The slurry obtained was stirred a further 1 h and then filtered. The filter pad was washed with dichloromethan (50 ml) and dired in vacuo to give the title compound as a white solid (4.95 g). M.p. 120–124° C. (decomposition).

Intermediate XII rel-(3R,3aS,6aR)-5-(4-Bromomethyl-benzoyl)-1-methanesulfonyl-3-propyl-hexahydro-pyrrolo[3,4-b]pyrrol-2-one Intermediate X (150 mg), 4-(bromomethyl) benzoyl chloride (161 mg) and sodium hydrogen carbonate (223 mg) were suspended in dichloromethane (15 ml) and stirred at room temperature overnight the mixture was diluted with dichloromethane, washed with saturated sodium hydrogen carbonate solution and evaporated to leave an orange solid from which the product was extracted using a pre-packed silica cartridge. The columns were eluted with vacuum suction using the following solvents; dichloromethane, chloroform, diethyl ether, ethyl acetate and acetonitrile to give the title compound as a cream solid (174 mg) Mass spec. MH$^+$ (found) 444, MH$^+$ (calc) 444.

Intermediate XIII

5-Formyl-isoxazole-3-carboxylic acid

A solution of ethyl-5-formylisoxazole-3-carboxylate (25 mg) in 1,4-dioxan (3 ml) and 2M hydrochloric acid (1 ml) was stirred and heated at reflux for 5 h.; cooled and the solvents removed in vacuo. The residue was triturated in diethyl ether. The solvent was removed and the residue dried to leave the title compound (18 mg) as an orange/brown solid.

T.l.c. (Silica, eluent dichloromethane:methanol 9:1) Rf=0.32.

Intermediate XIV rel-3-(1-Methanesulfonyl-2-oxo-3R-propyl-hexahydro-(3aS,6aR)-pyrrolo[3,4-b]pyrrole-5-carbonyl)-isoxazole-5-carbaldehyde Intermediate X (279 mg), Intermediate XIII (181 mg) and 1-(3-dimethylaminopropyl)-3-ethylcarbodiimide hydrochloride (378 mg) were dissolved in acetonitrile (30 ml) and the solution stirred at room temperature for 6 hours. The solvent was removed in vacuo, the residue dissolved in dichloromethane, washed with saturated sodium hydrogen carbonate and the product extracted using a pre-packed silica cartridge, eluting sequentially with dichloromethane, chloroform, diethyl ether, ethyl acetate, acetonitrile and methanol to leave the title compound as a white solid (216 mg). Mass spec MH$^+$ (found) 370, MH$^+$ (calc) 370.

EXAMPLES

Example 1 rel-(3R,3aS,6aR)-1-Methanesulfonyl-5-(4-piperidin-1-yl-but-2-enoyl)-3-propyl-hexahydro-pyrrolo[3,4-b]pyrrol-2-one hydrochloride Intermediate XI (0.44 g) was added at room temperature to a solution of Intermediate X (0.28 g) containing solid sodium hydrogen carbonate (0.34 g). The reaction was stirred for 4 h. The mixture was washed with saturated aqueous sodium hydrogen carbonate (20 ml). The aqueous phase was separated and extracted with dichloromethane (20 ml). The combined organics were washed with water (2×30 ml), dried over sodium sulphate and evaporated in vacuo. The resultant gum was purified by flash column chromatography on silica gel (Merck 9385) using gradient elution. The initial eluent, dichloromethane:ethanol:ammonia (200:8:1), was increased in polarity to dichloromethane:ethanol:ammonia (150:8:1). The resultant viscous oil (0.42 g) was dissolved in ethyl acetate (30 ml) and treated with ethereal hydrogen chloride. The resultant white solid suspension was evaporated and dried in vacuo to give the title compound. T.l.c. silica, dichloromethane:ethanol:ammonia (100:8:1); Rf. 0.55. Mass spec. MH$^+$ (found) 398, MH$^+$ (calc) 398.

Example 2 rel-(3R,3aS,6aR)-1-Methanesulfonyl-5-(4-piperidin-1-yl-butyryl)-3-propyl-hexahydro-pyrrolo[3,4-b]pyrrol-2-one A solution of Example 1 free base (0.2 g) in ethyl acetate 40 ml was stirred over a 10% palladium on carbon catalyst (0.1 g) under a hydrogen atmosphere at room temperature for 2 h. Hydrogen uptake 15 ml. The mixture was filtered through celite and the filtrate concentrated to ~15 ml. The concentrate was treated with ethereal hydrogen chloride (1M, 5 ml) precipitating a white solid. The mixture was evaporated and dried to give the title compound (0.15 g) as a white solid. Mass spec MH$^+$ (found) 400 MH$^+$ (calc) 400.

Example 3 rel-N-[4-(1-Methanesulfonyl-2-oxo-3R-propylhexahydro-(3aS,6aR)-pyrrolo[3,4-b]pyrrole-5-sulfonyl)-phenyl]acetamide Triethylamine (246 ml) and N-acetylsulfanilyl chloride (108 mg) were added to a solution of Intermediate X (100 mg) in dichloromethane (3.3 ml). The solution was stirred at room temperature for 5 h. Sodium hydrogen carbonate (150 mg) was added and the reaction stirred overnight. The resultant suspension was washed with saturated sodium hydrogen carbonate solution. The solvent was removed in vacuo. The resultant solid was purified using pre-packed silica cartridges. The columns were eluted with vacuum suction using the following solvents; dichloromethane (2×column volume), chloroform (2×column volume), diethyl ether (4×column volume), ethyl acetate (4×column volume) and acetonitrile (4×column volume) to give the title compound (48 mg) as a white solid. T.l.c. silica, dichloromethane:methanol, 9:1; Rf. 0.61. Mass spec. MH$^+$ (found) 444, MH$^+$ (calc) 444.

Example 4 rel-(3R,3aS,6aR)-1-Methanesulfonyl-5-(4-piperidin-1-ylmethyl-benzoyl)-3-propyl-hexahydro-pyrrolo[3,4-b]pyrrol-2-one hydrochloride Piperidine (47 mg) and sodium iodide (33 mg) were added to a solution of Intermediate XII (70 mg) in dichloromethane (5 ml) and the suspensions stirred at room temperature overnight. The reactions were washed with saturated sodium hydrogen carbonate solution and the products extracted using a pre-packed silica cartridge, eluting sequentially with dichloromethane, chloroform, diethyl ether, ethyl acetate, acetonitrile and methanol to leave a gum which was treated with ethereal hydrogen chloride and evaporated to leave the title compound as a yellow solid (44 mg).

T.l.c. (Silica, eluent dichloromethane:methanol 9:1) Rf=0.29.

Mass spec. MH+ (found) 448, MH+ (calc) 448.

The following Example was prepared in a similar manner to Example 4 from Intermediate XII:

Example 5 rel-(3R,3aS,6aR)-1-Methanesulfonyl-5-(4-morpholin-4-ylmethyl-benzoyl)-3-propyl-hexahydro-pyrrolo[3,4-b]pyrrol-2-one hydrochloride White solid T.l.c. (Silica, eluent dichloromethane:methanol 9:1) Rf=0.54.

Mass spec. MH+ (found) 450, MH+ (calc) 450.

Example 6 rel-(3R,3aS,6aR)-1-Methanesulfonyl-5-(5-morpholin-4-ylmethyl-isoxazole-3-carbonyl)-3-propyl-hexahydro-pyrrolo[3,4-b]pyrrol-2-one hydrochloride Morpholine was added to a solution of Intermediate XIV (50 mg) in dichloromethane (5 ml) and the solution stirred for two hours at room temperature. Sodium triacetoxyborohydride (43 mg) was added to the solution and the reaction stirred at room temperature overnight the reaction was washed with saturated sodium hydrogen carbonate solution and the product extracted using a pre-packed silica cartridge, eluting sequentially with dichloromethane, chloroform, diethyl ether, ethyl acetate, acetonitrile and methanol to leave a gum which was treated with ethereal hydrogen chloride and evaporated to leave the title compound as a white solid (24 mg).

T.l.c. (Silica, eluent dichloromethane:methanol 9:1) Rf=0.48.

Mass spec. MH+ (found) 441, MH+ (calc) 441.

The following Example was prepared in a similar manner to Example 6 from Intermediate XIV:

Example 7 rel-(3R,3aS,6aR)-5-(5-Dimethylaminomethyl-isoxazole-3-carbonyl)-1-methanesulfonyl-3-propyl-hexahydro-pyrrolo[3,4-b]pyrrol-2-one hydrochloride Yellow solid T.l.c. (Silica, eluent dichloromethane:methanol 9:1) Rf=0.40.

Mass spec. MH+ (found) 399, MH+ (calc) 399.

Biological Data

1. The compounds of Examples 1 to 7 were tested in the in vitro elastase test described earlier in the description. The $IC_{50}$ values are given in the table below:

| Example | $IC_{50}$ ($\mu$M) |
|---------|---------|
| 1 | 0.227 |
| 2 | 0.9 |
| 3 | 0.229 |
| 4 | 0.296 |
| 5 | 0.222 |
| 6 | 0.146 |
| 7 | 0.399 |

What is claimed is:
1. A compound of formula (I)

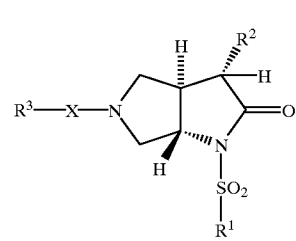

(relative stereochemistry indicated)
wherein:
$R^1$ represents $C_{1-6}$alkyl;
$R^2$ represents $C_{2-4}$alkyl or $C_{2-4}$alkenyl;
X represents CO or $SO_2$;
$R^3$ represents:
(a) $C_{2-8}$alkenyl $NR^4R^5$;
(b) phenyl substituted by $(CH_2)_aQ(CH_2)_bNR^4R^5$
(c) a 5 or 6 membered heterocyclic aromatic ring containing 1 or 2 heteroatoms selected from N, S and O substituted by $(CH_2)_aQ(CH_2)_bNR^4R^5$;
(d) phenyl substituted by $NHCOC_{1-8}$alkyl;
(e) a group as defined in (b), (c), or (d) further substituted on the phenyl or heterocyclic ring by one or more groups selected from $C_{1-4}$alkyl, $C_{1-4}$alkoxy, halogen and nitro; or
(f) $C_{1-8}$alkyl$NR^4R^5$;
$R^4$ and $R^5$ independently represent hydrogen, $C_{1-8}$alkyl, —$(CH_2)_{1-4}CONR^6R^7$, $COC_{1-4}$alkyl or $(CH_2)_{0-2}$ Ph where Ph represents phenyl optionally substituted by one or more $C_{1-4}$alkyl or halogen groups or $NR^4$ $R^5$ together represents azetidinyl, pyrrolidinyl, piperidinyl, azepinyl, morpholinyl, piperazinyl or N—$C_{1-6}$alkyl-piperazinyl or such a heterocyclic ring optionally substituted by one or more $C_{1-4}$alkyl, $CONR^6R^7$ or $COOR^6$ groups;
Q represents a bond, S, O or $NR^8$;
a represents 0 to 4 and b represents 2 to 4 save that a+b lies in the range 2 to 6 except when Q represents a bond in which case b may also represent 0 or 1 and a+b may lie in the range 0 to 6;
$R^6$, $R^7$ and $R^8$ independently represent hydrogen or $C_{1-4}$alkyl;
and salts and solvates thereof.
2. A compound of formula I as defined in claim 1 wherein $R^3$ represents:
(a) $C_{2-8}$alkenyl $NR^4R^5$;
(b) phenyl substituted by $(CH_2)_aQ(CH_2)_bNR^4R^5$;
(c) a 5 or 6 membered heterocyclic aromatic ring containing 1 or 2 heteroatoms selected from N, S and O substituted by $(CH_2)_aQ(CH_2)_bNR^4R^5$;

(d) phenyl substituted by $NHCOC_{1-8}$alkyl; or (e) a group as defined in (b), (c), or (d) further substituted on the phenyl or heterocyclic ring by one or more groups selected from $C_{1-4}$alkyl, $C_{1-4}$alkoxy, halogen and nitro.

3. A compound of formula (I) as defined in claim 1 wherein $R^3$ represents (a) $C_{2-8}$alkenyl $NR^4R^5$;

(b) phenyl substituted by $(CH_2)_aQ(CH_2)_bNR^4R^5$;

(c) a 5 or 6 membered heterocyclic aromatic ring containing 1 or 2 heteroatoms selected from N, S and O substituted by $(CH_2)_aQ(CH_2)_bNR^4R^5$; or (d) a group as defined in (b) or (c) further substituted on the phenyl or heterocyclic ring by one or more groups selected from $C_{1-4}$alkyl, $C_{1-4}$alkoxy, halogen and nitro.

4. A compound of formula (I) according to claim 1 wherein X represents CO.

5. A compound of formula (I) according to claim 1 wherein $R^2$ represents isopropyl or propyl.

6. A compound of formula (I) according to claim 5 wherein $R^2$ represents isopropyl.

7. A compound of formula (I) according to any claim 1 wherein $R^1$ represents methyl or ethyl.

8. A compound of formula (I) according to claim 7 wherein $R^1$ represents methyl.

9. A compound of formula (I) which is:

rel-(3R,3aS,6aR)-1-Methanesulfonyl-5-(4-piperidin-1-yl-but-2-enoyl)-3-propyl-hexahydro-pyrrolo[3,4-b]pyrrol-2-one;

rel-(3R,3aS,6aR)-1-Methanesulfonyl-5-(4-piperidin-1-yl-butyryl)-3-propyl-hexahydro-pyrrolo[3,4-b]pyrrol-2-one;

rel-N-[4-(1-Methanesulfonyl-2-oxo-3R-propylhexahydro-(3aS,6aR)-pyrrolo[3,4-b]pyrrole-5-sulfonyl)-phenyl]acetamide;

rel-(3R,3aS,6aR)-1-Methanesulfonyl-5-(4-piperidin-1-ylmethyl-benzoyl)-3-propyl-hexahydro-pyrrolo[3,4-b]pyrrol-2-one;

rel-(3R,3aS,6aR)-1-Methanesulfonyl-5-(4-morpholin-4-ylmethyl-benzoyl)-3-propyl-hexahydro-pyrrolo[3,4-b]pyrrol-2-one;

rel-(3R,3aS,6aR)-1-Methanesulfonyl-5-(5-morpholin-4-ylmethyl-isoxazole-3-carbonyl)-3-propyl-hexahydro-pyrrolo[3,4-b]pyrrol-2-one;

rel-(3R,3aS,6aR)-5-(5-Dimethylaminomethyl-isoxazole-3-carbonyl)-1-methanesulfonyl-3-propyl-hexahydro-pyrrolo[3,4-b]pyrrol-2-one;

or a salt or solvate of any one thereof.

10. A purified single enantiomer of a compound of formula (I) according to claim 1 having the absolute stereochemistry as illustrated in formula (I).

11. A compound of formula (I) according to claim 1 for use as a pharmaceutical.

12. A pharmaceutical composition comprising a compound of formula (I) according to claim 1 in admixture with one or more physiologically acceptable diluents or carriers.

13. A method of treatment of chronic bronchitis in a human or animal subject which comprises administering to said human or animal subject an effective amount of a compound of formula (I) according to claim 1.

\* \* \* \* \*